US006281169B1

(12) United States Patent
Yeoman et al.

(10) Patent No.: US 6,281,169 B1
(45) Date of Patent: Aug. 28, 2001

(54) AQUEOUS SUSPENSIONS OF LOW SOLUBILITY AND LOW STABILITY WATER ADDITIVES

(75) Inventors: Alan M. Yeoman, Duluth, GA (US); Frederick A. Grunewald, New Braunfels, TX (US); Jonathan N. Howarth, Baton Rouge, LA (US); Alan D. Harrison, Douglasville, GA (US); Brian R. Sook, Snellville, GA (US); Thomas Kruppa, Newport, TN (US)

(73) Assignee: BioLab Services, Inc., Wilmington, DE (US)

( * ) Notice: Subject to any disclaimer, the term of this patent is extended or adjusted under 35 U.S.C. 154(b) by 0 days.

(21) Appl. No.: 09/363,457

(22) Filed: Jul. 29, 1999

(51) Int. Cl.$^7$ .......................... A01N 25/30; A01N 33/18; A01N 43/10; A01N 43/66; A01N 59/06
(52) U.S. Cl. .......................... 504/150; 504/151; 504/154; 504/155; 504/156; 504/363
(58) Field of Search .................................... 504/150, 151, 504/154, 155, 156, 363

(56) References Cited

U.S. PATENT DOCUMENTS

| 4,051,055 | * | 9/1977 | Trinh et al. | 252/95 |
| 4,941,988 | * | 7/1990 | Wise | 252/99 |
| 5,376,297 | * | 12/1994 | Choy et al. | 252/108 |
| 5,730,996 | * | 3/1998 | Beall et al. | 4724/405 |

* cited by examiner

*Primary Examiner*—S. Mark Clardy
(74) *Attorney, Agent, or Firm*—Woodard, Emhardt, Naughton, Moriarty & McNett (57) ABSTRACT

A method of improving the rate of dissolution in water of low solubility compounds by combining a low solubility compound with a rheology additive that is made of platelets or particles which orient together with ionic or hydrogen bonds. The inventive method also may improve the hydrolytic stability of hydraulically unstable low solubility compounds.

60 Claims, 1 Drawing Sheet

AQUEOUS SUSPENSIONS OF LOW SOLUBILITY AND LOW STABILITY WATER ADDITIVES

FIELD OF THE INVENTION

The present invention relates generally to compounds such as biocides that have poor solubility and/or stability in water, and more particularly to methods and compositions for improving the stability and/or dissolution rate of such compounds.

BACKGROUND TO THE INVENTION

Many compounds that have low solubility in water (e.g., compounds that have a solubility of less than 1%) have other properties that make them particularly appropriate for use in aqueous systems. For example, many solid halogen donor materials such as halogenated hydantoins have low solubility, but are effective and economical biocides for recreational and industrial water systems. Similarly, non-biocides such as cyanuric acid have low solubility but are effective UV stabilizers for halogen source materials.

More particularly describing the halohydantoins, solid halohydantoins such as bromochlorodimethylhydantoin (BCDMH) have been used to sanitize waters for many years. Unfortunately though, many solid halogen donors and all of the halohydantoins have low water solubility, slow dissolving kinetics and are hydrolytically unstable. The water solubility for BCDMH, for example, is low, approximately 1,500 mg/liter at 20° C., and it dissolves slowly, depending on surface area, contact time and water temperature.

Moreover, dissolved BCDMH is not hydrolytically stable because it hydrolyses to yield dimethylhydantoin and the biocidal hypohalous acids, hypochlorous acid and hypobromous acid, which in turn degrade to the respective halides, chloride and bromide, within hours.

Solid halogen donors are available as solids in powdered form and also in various compressed forms such as granules, tablets or briquettes. These are dosed to treated water systems by several means, each of which is labor intensive and exposes workers to the solid product. Among the dosing methods are:

1. Manual broadcasting of product onto the water surface with product dissolving directly in the system. The amount of product used in the broadcasting system can be accurately measured. However, the rate at which the product dissolves will vary with water temperature, mixing and product form. If the product dissolves too slowly, the concentration in the system water may not reach a high enough level to be effective. Locally high concentrations and undissolved product in contact with system parts can cause compatibility problems in some systems.

2. Submerged porous containers or product in the water with product dissolving directly in the system. This approach eliminates direct contact of the product with system parts but there may still be problems associated with locally high concentrations. It is more difficult to control how much product dissolves in the system with this method because the concentration will be dependent on water temperature, mixing and product form so the product may be overdosed or underdosed.

3. Bypass feeders use a fresh, or system, water stream to dissolve product by passing through a product bed in the feeder. This concentrated solid halogen solution is subsequently diluted into the system being treated. This method typically eliminates system material compatibility problems. However, feed consistency does vary with bypass water temperature, contact time (feeder volume, water flow and quantity of product in the bed) and product form. The level of product in the bypass feeder must be maintained for consistent feed and the water flow rates need to be adjusted to compensate for any temperature variations. There may be problems associated with extra water being added to some systems if system water is inappropriate for use in the bypass feeder.

4. Slurry feed is a method where product is mixed with a fresh, or system, water stream to create a slurry (typically less than 3% of the solid halogen donor) which is subsequently diluted into the system. This method can very accurately meter the required quantity of product and eliminates dependence on water temperatures or very accurate control of water flow rate. This equipment can be expensive and there may be problems associated with extra water being added to some systems if system water is inappropriate for the bypass stream.

As to some other low solubility water additives that are appropriate for use in the present invention, terbuthylazine, [2-(tert-butylamino)-4-chloro-6-(ethylamino)-s-triazine], is used as an algae control agent in water either alone or, synergistically, with oxidizing halogen. More detail regarding this type of application may be found, for instance, in *Impact of Cooling Water Treatment Trends on Algae Control* by J. F. Kramer Off Proc.—Int. Water Conf. (1995),56$^{th}$, 449–456. It is also useful for stabilizing halogen in water systems as described in EP 857694 *Method for Stabilizing Disinfectant in Aqueous System*, by J. F. Kramer and F. O'Brien (1998).

The US-EPA Registration Eligibility Decision (RED) document published in December 1997 (available electronically at www.EPA.gov) indicated that the solubility for terbuthylazine is 11.5 ppm at 25° C. with use levels between 1 and 9 ppm. Terbuthylazine has good hydrolytic stability with degradation half lives of 73 days at pH 5,205 days at pH 7 and 194 days at pH 9.

The product is available as a 96% wettable powder (Bellacide® 320), as well as a 44.7% aqueous dispersion (Belclene® 329) and a 4% aqueous dispersion (Bellacide® 325). The product brochure from FMC entitled *Bellacide® 325 An Effective Algal control Agent Recommended for Recirculating Cooling Water Systems and Decorative Fountains* recommends product addition at a point in the system where there is good mixing such as in the cooling tower sump near the recirculating pump.

It would be advantageous if an easily pumped concentrated aqueous formulation of terbuthylazine were available with an improved rate of dissolution, because the solubility limit for terbuthylazine (11.5 ppm) is so close to the required treatment range (1 ppm to 9 ppm).

As to other low solubility biocides, 2-(2-bromo-2-nitro)-ethenyl furan (hereinafter BNEF) is useful for controlling algal, fungal and bacterial growth in water systems. Its manufacture and use have been described in several U.S. Pat. Nos. such as 4,965,377; 5,138,078; 5,090,990; 5,045,104; 5,246,943; 5,358,963; 5,416,107 and 5,416,108. BNEF decomposes rapidly in water; at 25° C. the decomposition half-life is 71 hours at pH5, 37 hours at pH 6 and 6 hours at pH 9. Decomposition occurs even faster at higher temperatures; at pH 4 the decomposition half-life is 140 minutes at 50° C., 106 minutes at 60° C. and 49 minutes at 70° C. Even though BNEF is not very hydrolytically stable, this non-oxidizing biocide kills rapidly so that it is effective if the proper amount can be dissolved in water. However, this material is only marginally soluble in water, 300 ppm at 25° C. This low water solubility, along with rapid decomposition can make it difficult dissolve the desired level of active ingredient. U.S. Pat. No. 5,122,301 by McCoy et. al. describes the preparation of a soluble formulation containing 10% BNEF in an organic solvent, propylene carbonate. Dosing systems with BNEF with this formulation will result in organic contamination.

It would be advantageous if an easily pumpable concentrated aqueous formulation of BNEF were available with a rapid dissolved rate.

As to non-biocidal water additives with low solubility, Isocyanuric Acid (hereinafter "CYA," and also referred to as S-triazine-2,4,6-trione), is used in water treatment to stabilize oxidizing halogen against decomposition. This is described in the *Professional Pool an Spa Technicians' Guide to Chlorine* by R. W. Lowry and D. Dickman (1989), Service Industry Publications, Inc. This publication suggests adding CYA granules by sifting or broadcasting them over the surface of the deep end of the pool. It states that the granules are fairly tough to dissolve and often sit on the bottom of the pool for as long as a week. Alternatively, the granules can be "dissolved" in warm water with soda ash and added to the pool by "walking" the solution around the pool.

The solubility of CYA in water is approximately 2700 ppm at 20° C. CYA is typically supplied as a 99% to 100% pure granular material. In addition to water treatment, CYA has uses as a chemical intermediate in the manufacture of resins, plastics additives and coatings. For the reasons noted above, it would be advantageous if easily pumped, rapidly dissolving concentrated aqueous formulations of CYA were available.

As indicated above however, it is impractical to prepare aqueous solutions of the above-mentioned water additives (and others with similar characteristics) because these products exhibit low water solubility, slow dissolving kinetics and are hydrolytic unstable. Moreover, many organic solvents are not compatible with solid halogen donors, and even if they were, it is undesirable to add organic solvents to water systems because they contaminate the water, contribute to undesirable biological activity, and require additional waste water treatment prior to discharge.

In view of the above a need continues to exist for concentrated aqueous dispersions of low solubility and/or low stability water additives. The present invention addresses that need.

SUMMARY OF THE INVENTION

Briefly describing one aspect of the present invention, there is provided a method of improving the rate of dissolution in water of low solubility compounds. The preferred method comprises combining a low solubility compound with a rheology additive that is made of platelets or particles that orient together with ionic or hydrogen bonds. The suspension formed thereby can be added to water to improve the rate of dissolution of the low solubility compound.

In another aspect of the present invention, there is provided a method of improving the hydrolytic stability of certain hydraulically unstable compounds. The preferred method comprises combining a hydraulically unstable compound with a rheology additive that is made of platelets or particles, which orient together with ionic or hydrogen bonds. The suspension formed thereby has improved hydrolytic stability when compared to the untreated compound.

One object of the present invention is to provide improved methods for providing low solubility compounds to aqueous systems.

Further objects and advantages of the present invention will be apparent from the following description.

BRIEF DESCRIPTION OF THE INVENTION

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the described embodiments, and such further applications of the principles of the invention as described herein, being contemplated as would normally occur to one skilled in the art to which the invention pertains.

As indicated above, the present invention makes improved aqueous preparations of substances which exhibit one or more of the following characteristics:

1. low water solubility which limits the percentage of the substance which can be included in aqueous solution preparations, or 2. poor hydrolytic stability which limits storage life of the substance in aqueous preparations, or 3. poor dissolving behavior, such as slow dissolution rates or oil formation, at use concentrations The inventive preparations, which may either be made on site or pre-manufactured, are thickened suspensions that exhibit one or more of the following improvements:

1. reduction or elimination of organic solvents and the problems associated therewith;

2. simplified handling and feeding, thereby reducing labor requirements and worker exposure, and improve dosing accuracy and consistency; and 3. improved dispersion/dissolving behavior, resulting in the ability to feed the preparation directly to the application or with dilution water, and providing more rapid and complete dissolution allowing higher and more immediate dosing.

More particularly describing the compounds which may advantageously be used in the present invention, one aspect of the invention improves the performance of compounds that would be useful as water additives, but which have low solubility in water. For the purposes of this invention, solubility in water of less than about 1% is considered to be low solubility.

Another aspect of the present invention improves the performance of water additives that have poor hydrolytic stability. For the purposes of this description, poor hydrolytic stability is indicated when the additive has a decomposition half-life of less than about seven (7) days.

Among the compounds that may be used in the present invention are bromochlorodimethylhydantoin (BCDMH); bromonitroethenylfuran (BNEF), bromonitrostyrene (BNS), terbuthylazine (TBZ), cyanuric acid (CYA), trichloroisocyanuric acid (TCCA), dichloroisocyanuric acid (DCCA), dibromodimethylhydantoin (DBDMH), dichlorodimethylhydantoin (DCDMH), dichloromethylethylhydantoin (DCMEH), methylene-bis-thiocyanate (MBT), and solid metal hypohalites such as calcium hypochlorite. All of these compounds exhibit low solubility and/or poor hydrolytic stability and/or a poor rate of dissolution in aqueous systems.

As to the amount of water additive present in the inventive aqueous suspension, it will be appreciated by the art that the appropriate amount will depend on the specific additive being employed, and the desired use of that additive. In general terms though, amounts of between 1% and 80% may advantageously be used, with amounts between about 20% to about 60% being more preferred. In the most preferred embodiments, the additive preferably comprises about 40% of the aqueous suspension.

Among the rheology additives that may be used in the present invention are natural clays such as smectite, synthetic clays such as synthetic smectite, natural aluminas, synthetic aluminas, natural silicas, synthetic silicas, and organic dispersants. In the more preferred embodiments commercially available a synthetic smectite (e.g., Laponite®, from Southern Clay Products), or a natural smectite (e.g., Van Gel from R.T. Vanderbilt Company, Inc.) is used.

As indicated above, the rheology additives comprise platelets or particles that orient together with ionic or hydrogen bonds to form three-dimensional structures. This structure formation is reversible due to the relatively weak nature of the bonds, so that when the bonds are disrupted by shearing action the structure comes apart, but re-establishes when the composition is at rest. In the most preferred embodiments the rheology additive consists essentially of such platelets or particles.

It can be seen from the above that the preferred rheology additives are thixotropic. This is an additional benefit when it is desired to pump the compositions.

As to the amount of the rheology additive used to make the aqueous suspension, preferably the suspension comprises about 0.1% to about 10% rheology additive. In the more preferred embodiments about 0.5% to about 5% rheology additive is used. Most preferably, about 1% to about 4% rheology additive is present in the aqueous suspension.

One preferred rheology additive is the natural smectite marketed under the trade name Van Gel by R.T. Vanderbilt Company, Inc. When Van Gel is used the rheology additive preferably comprises about 2% to about 4% of the aqueous suspension.

Another preferred rheology additive is the synthetic smectite marketed under the trade name Laponite® by Southern Clay Products, Inc. When Laponite® is used the rheology additive preferably comprises about 0.5% to about 3% of the aqueous suspension.

Another preferred rheology additive is the synthetic alumina marketed under the trade name Dispal® by the Vista Chemical Company. When Dispal® is used the rheology additive preferably comprises about 1% to about 5% of the aqueous suspension.

Another preferred rheology additives is the fumed silica marketed under the trade name Cab-O-Sil by Cabot Corporation. When Cab-O-Sil is used the rheology additive preferably comprises about 0.1% to about 10% of the aqueous suspension.

It is to be appreciated that several rheology additives may be used in combination. For example, a synthetic smectite such as Laponite® may be combined with a synthetic alumina such as Dispal® to provide the desired rheology additive.

The selection of the rheology additive may also be made to optimize other performance characteristics such as the stability of the aqueous suspension when frozen and thawed. For example, natural smectite rheology additives such as Van Gel-O have been found to provide significant freeze/thaw stability to the aqueous suspensions of the present invention.

Reference will now be made to specific examples using the processes described above. It is to be understood that the examples are provided to more completely describe preferred embodiments, and that no limitation to the scope of the invention is intended thereby.

EXAMPLE 1

The dissolution rate of BromiCide® Powder (approximately 96% bromochlorodimethylhydantoin, BCDMH, available from BioLab, Inc.) was determined by analyzing filtered samples over time from a stirred BromiCide Powder/water preparation. The time required to dissolve 90% of the BCDMH was calculated from a fit of the data. The biocidal efficacy of dissolved BCDMH against bacteria was compared with sodium hypochlorite at similar free halogen concentrations.

The BCDMH assay of BromiCide Powder was determined by adding a known amount, approximately 0.1 grams of BromiCide Powder, into 80 milliliters of water, stirring vigorously with a magnetic stirrer for approximately two minutes followed by filtration through a 0.45 micron filter. The total oxidizing halogen content of this filtrate was determined after the addition of potassium iodide (KI) and acetic acid by potentiometric titration with standardized (0.10 N) sodium thiosulfate. The result of this titration was used to calculate the percent BCDMH present in BromiCide Powder.

One liter of water in a 1 liter beaker was magnetically stirred using a two inch magnetic stir bar at a slow rate (setting 5 on a Thermodyne Nuova II magnetic stirrer). The 400 mg BCDMH/l target concentration was established by adding a known amount, approximately 0.4 grams, of assayed BromiCide Powder to the stirring water. The nominal BCDMH concentration was calculated from the actual amount of BromiCide Powder used and its assay. Samples of this preparation, taken over time, were immediately filtered through a 0.45 micron filter. The concentration of total oxidizing halogen in the filtrate, determined by potentiometric titration using standardized (0.01 N) sodium thiosulfate, was used to calculate the dissolved BCDMH concentration. Dissolved BCDMH concentration was expressed in Table 1 as a percentage of the nominal concentration.

TABLE 1

| BCDMH Powder Dissolution Rate | | | | | | | | | | | |
| --- | --- | --- | --- | --- | --- | --- | --- | --- | --- | --- | --- |
| Minutes | 0.5 | 1.0 | 1.5 | 2.0 | 3.0 | 5.5 | 8.0 | 10.5 | 20.0 | 45.5 | 52.0 |
| % Dissolved | 11.1 | 17.0 | 21.7 | 25.8 | 31.8 | 40.9 | 51.0 | 57.2 | 74.4 | 89.7 | 91.8 |

Figure 1:
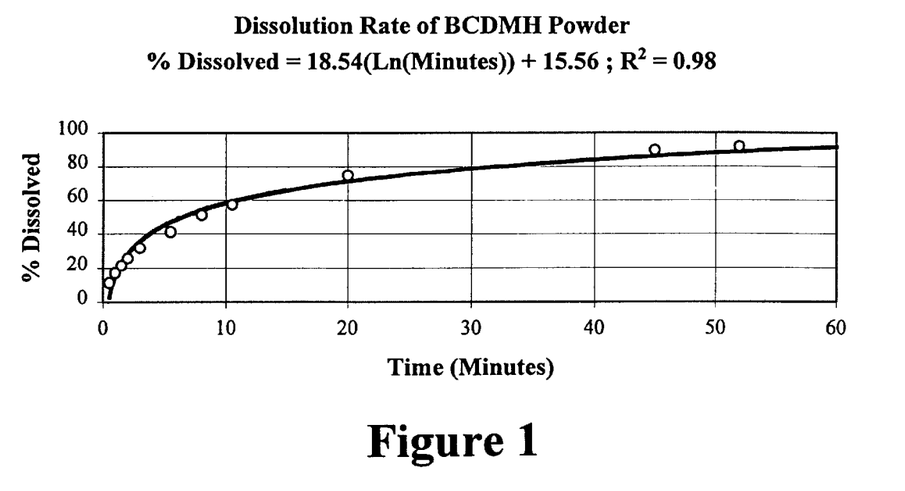
FIG. 1 shows the dissolution rate of BCDMH powder.

This data was fit as shown in FIG. 1, by the method of least squares, to the following equation: % Dissolved=M×{Ln(Minutes)}+B. For this case; M=18.54, B=15.56 with $R^2$=0.98. The calculated time to reach 90% of the nominal concentration was 55.4 minutes.

The biocidal efficacy of dissolved BCDMH was compared to sodium hypochlorite using AOAC Official Method 965.13 (1995 Edition)—*Disinfectant (Water) for Swimming Pools* against the gram-negative bacteria *E. coli* (ATCC #11229) and the gram-positive bacteria *Strep. faecalis* (ATCC #6569). The desired nominal biocide dosage (0, 0.1, 0.3, 0.6 or 0.9 mg/l total halogen expressed as chlorine) was established by dilution from freshly prepared (filtered) standardized stock solutions of either BCDMH Powder or NaOCl into phosphate buffered water (approximate pH of 7.5 as described in the method). An inoculum was standardized to yield $2×10^8$ organisms per ml. One ml of the standardized inoculum was mixed into 199 ml of phosphate buffered water containing the desired dosage of biocide. One-ml aliquots were removed at specific times (30, 60, 120 and 180 seconds after inoculum addition) and added, with mixing, into separate tubes containing 9 ml of thiosulfate solution to neutralize the oxidizing halogen. Five 1 ml aliquots of from each neutralization tube were then added and mixed into five separate tubes each containing 9 ml of subculture broth. After 48 hours of incubation, these were examined to determine growth or no growth in the subculture medium. Results given in Table 2 are expressed as the number of tubes (out of the five possible) that exhibit growth after incubation. The efficacy of NaOCl and dissolved BCDMH in this test are approximately the same at equivalent total oxidizing halogen levels.

TABLE 2

Efficacy Comparison: NaOCl and BCDMH Powder

| | | Number of Tubes (Out of 5) Exhibiting Growth | | | | | | | |
|---|---|---|---|---|---|---|---|---|---|
| ppm † | | *E. coli* | | | | *Strep. Faecalis* | | | |
| Total Halogen | Biocide Treatment | 30 sec | 60 sec | 120 sec | 180 sec | 30 sec | 60 sec | 120 sec | 180 sec |
| 0.0 | None | 5 | 5 | 5 | 5 | 5 | 5 | 5 | 5 |
| 0.1 | NaOCl | 5 | 5 | 5 | 5 | 5 | 5 | 5 | 5 |
| 0.3 | NaOCl | 5 | 5 | 3 | 1 | 5 | 5 | 5 | 5 |
| 0.6 | NaOCl | 0 | 0 | 0 | 0 | 0 | 0 | 0 | 0 |
| 0.1 | BCDMH | 5 | 5 | 5 | 5 | 5 | 5 | 5 | 5 |
| 0.3 | BCDMH | 5 | 5 | 5 | 5 | 5 | 5 | 4 | 1 |
| 0.6 | BCDMH | 0 | 0 | 0 | 0 | 0 | 0 | 0 | 0 |
| 0.9 | BCDMH | 0 | 0 | 0 | 0 | 0 | 0 | 0 | 0 |

† ppm expressed as $Cl_2$

EXAMPLE 2

The dissolution rate, accelerated storage stability and ease of pumping of a 40% BCDMH preparation were determined.

A preparation was made by mixing 417 grams of Bromi-Cide Powder, 3 grams of monobasic potassium phosphate ($KH_2PO_4$) into 580 grams of water using a high shear mixer (Caframo BDC 6015 mixer with a 3 inch High shear dispersing impeller operated at approximately 800 rpm.).

The assay of the resulting preparation was determined as described in Example 1 except that approximately 0.2 grams of the preparation is initially dissolved in the 80 ml of water rather than 0.1 grams of powder because the preparation is approximately 40% BCDMH.

The dissolution rate of the BCDMH in this preparation was determined as described in Example 1 except that the 400 mg BCDMH/l target was established by adding a known amount of approximately 1.0 gram of the preparation to 1 liter of water. The calculated time to reach 90% of the nominal concentration was 3.9 minutes with a good fit ($R^2$=0.97). Pre-wetting the powder in this preparation resulted in much faster dissolution (93% improvement) compared to dry powder in Example 1.

Accelerated storage stability was determined by comparing the initial assay to the assay of the preparation after 15 and 30 days storage at 50° C. (122° F.). The results are reported as percent relative activity loss where:

% Relative Activity Loss={(Initial Assay—Current Assay)/(Initial Assay)}×100. For example a preparation with an Initial Assay of 40% BCDMH would have a 10% relative activity loss when the current assay was 36% BCDMH. For this preparation the relative activity loss was 17.0% at 15 days and 21.0% at 30 days.

Pumping performance was tested using a diaphragm metering pump in suction lift mode. A 4 liter graduated cylinder containing approximately 4 kg of the preparation was placed on the floor. A diaphragm pump (pump model—Alpha 080NP6060D0, available from ProMinent Fluid Controls Inc.) was mounted 4 feet (122 cm) above the floor with the semi-rigid tubing from the suction side of the pump inserted into the preparation. The pump was discharged into a 4 liter beaker. Pumping performance was poor. Pumping dewatered and thickened the material in the graduated cylinder to the point where it would no longer pump.

This preparation dissolved more rapidly than dry BCDMH powder probably because of pre-wetting. This preparation was not a stable suspension, the shelf life as measured by accelerated storage testing was poor and suction lift pumping caused dewatering.

EXAMPLE 3

The dissolution rate, accelerated storage stability and ease of pumping a 40% BCDMH preparation were determined.

A preparation was made by mixing 417 grams of Bromi-Cide Powder, 4 grams of boric acid ($H_3BO_3$) and 10 grams of the Laponite® RD (available from Southern Clay Products), a synthetic hectorite clay thickening and suspending agent, with 569 grams of water using a high shear mixer as described in Example 2.

The dissolution rate of the BCDMH in this preparation was determined as described in Example 2. The calculated time to reach 90% of the nominal concentration was 1.4 minutes with a good fit ($R^2$=0.96). This preparation exhibited even more rapid dissolution than the pre-wetted powder preparation from Example 2.

Accelerated storage stability was determined for this preparation as described in Example 2. For this preparation the relative activity loss was 12.0% at 15 days and 17.7% at 30 days. This represents a significant improvement over wetted powder at the 15 day point with a more modest improvement at 30 days.

Pumping performance was tested using a diaphragm metering pump in suction lift mode as described in Example 2. Pumping performance was improved compared to the preparation in Example 2, however the pump rates were not consistent over the entire test.

The addition of the synthetic clay dispersing and thickening agent resulted in several surprising improvements over the wetted BCDMH Powder preparation from Example 2. Dissolution was even more rapid for this preparation than for the pre-wetted powder preparation from Example 2.

Relative activity loss was also improved compared to the preparation in Example 2. In addition, there is improved physical stability of the suspension compared to the preparation from Example 2 based on reduced separation during the pumping.

EXAMPLE 4

The dissolution rate, accelerated storage stability and ease of pumping a 40% BCDMH preparation were determined.

A preparation was made by mixing 417 grams of Bromi-Cide Powder, 3 grams of monobasic potassium phosphate ($KH_2PO_4$) and 30 grams of the Dispal® 23N4-80 (available from Condea-Vista), a synthetic alumina thickening and suspending agent, with 550 grams of water using a high shear mixer as described in Example 2.

The dissolution rate of the BCDMH in this preparation was determined as described in Example 2. The calculated time to reach 90% of the nominal concentration was 3.3 minutes with a good fit ($R^2$=0.99). This preparation exhibited slightly more rapid dissolution than the pre-wetted powder preparation from Example 2, but slower dissolution than the preparation from Example 3.

Accelerated storage stability was determined for this preparation as described in Example 2. For this preparation the relative activity loss was 4.5% at 15 days and 9.2% at 30 days. This is an improvement over the performance of the preparation form Example 2.

Pumping performance was tested using a diaphragm metering pump in suction lift mode as described in Example 2. The flow of material was not consistent, the preparation stopped flowing before the test was completed.

The addition of the synthetic alumina dispersing and thickening agent resulted in several surprising improvements over the wetted BCDMH Powder preparation from Example 2. Relative activity loss was significantly improved compared to the preparation in Example 2 and was superior to the preparation described in Example 3. Dissolution was slightly more rapid for this preparation than for the pre-wetted powder preparation from Example 2, but slower than the preparation from Example 3. Although the preparation did not continue to flow throughout the test, it did not dewater indicating better dispersion stability than seen in Example 2.

EXAMPLE 5

The dissolution rate, accelerated storage stability and biocidal efficacy of a 40% BCDMH preparation combining the thickening and suspending agents from Examples 3 and 4 were determined. A combination of two synthetic clays was used in this Example because it was found that this gave a smoother texture than when only one synthetic clay was used.

A preparation was made by mixing 417 grams of Bromi-Cide Powder, 3 grams of monobasic potassium phosphate ($KH_2PO_4$), 3 grams of the Laponite® RD and 9 grams of Laponite® RDS (both synthetic hectorite clay thickening and suspending agents available from Southern Clay Products), and 10 grams of Dispal® 23N4-80 (a synthetic alumina thickening and dispersing agent available from Condea-Vista) with 558 grams of water using a high shear mixer as described in Example 2.

The dissolution rate of the BCDMH in this preparation was determined as described in Example 2. The calculated time to reach 90% of the nominal concentration was 1.6 minutes with a good fit ($R^2$=0.93). This preparation exhibited dissolution rates similar to the preparation from Example 3.

Accelerated storage stability was determined for this preparation as described in Example 2. For this preparation the relative activity loss was 12.5% at 15 days and 17.4% at 30 days. This is approximately equivalent to the results from Example 3.

The efficacy of this preparation was tested as described in Example 1 except that no stock solution of the preparation was made. The appropriate amount of assayed preparation was added directly to the buffer solution immediately before the inoculun was added. This was done to determine whether the preparation would release BCDMH rapidly at use level to achieve kill or if there would be a delay due to slow dissolution. The results in Table 3 indicate that efficacy is equivalent to predissolved BCDMH.

TABLE 3

Efficacy Comparison: BCDMH Powder and Example 5

| | | Number of Tubes (Out of 5) Exhibiting Growth | | | | | | | |
|---|---|---|---|---|---|---|---|---|---|
| ppm † | | E. coli | | | | Strep. Faecalis | | | |
| Total Halogen | BCDMH Treatment | 30 sec | 60 sec | 120 sec | 180 sec | 30 sec | 60 sec | 120 sec | 180 sec |
| 0.0 | None | 5 | 5 | 5 | 5 | 5 | 5 | 5 | 5 |
| 0.1 | Powder | 5 | 5 | 5 | 5 | 5 | 5 | 5 | 5 |
| 0.3 | Powder | 5 | 5 | 5 | 5 | 5 | 5 | 4 | 1 |
| 0.6 | Powder | 0 | 0 | 0 | 0 | 0 | 0 | 0 | 0 |
| 0.9 | Powder | 0 | 0 | 0 | 0 | 0 | 0 | 0 | 0 |
| 0.1 | Example 5 | 5 | 5 | 5 | 5 | 5 | 5 | 5 | 5 |
| 0.3 | Example 5 | 5 | 5 | 5 | 5 | 5 | 5 | 5 | 5 |
| 0.6 | Example 5 | 0 | 0 | 0 | 0 | 0 | 0 | 0 | 0 |
| 0.9 | Example 5 | 0 | 0 | 0 | 0 | 0 | 0 | 0 | 0 |

† ppm expressed as $Cl_2$ - BCDMH Powder results are also found in Example 1

It was surprisingly found in this example that biocidal efficacy was essentially the same as when predissolved BCMDH was used. This indicates that the dispersing and thickening agents are not inhibiting the release of BCDMH when diluted to use level. This combination of synthetic clay and synthetic alumina from the previous examples showed that, at this level, the alumina did not negatively effect the superior dissolution rate associated with the synthetic clay only formula from Example 3. The addition of the alumina at this lower level did not significantly improve the accelerated storage stability of the preparation.

EXAMPLE 6

The dissolution rate, accelerated storage stability and biocidal efficacy of a 40% BCDMH preparation was determined. The method was similar to that of Example 5 except that dimethylhydantoin (DMH) was added in an attempt to improve accelerated storage stability performance.

A preparation was made by mixing 417 grams of Bromi-Cide Powder, 3 grams of monobasic potassium phosphate ($KH_2PO_4$), 3 grams of the Laponite® RD and 9 grams of Laponite® RDS (both synthetic hectorite clay thickening and suspending agents available from Southern Clay Products), 10 grams of Dispal® 23N4-80 (a synthetic alumina thickening and dispersing agent available from Condea-Vista) and 100 grams of dimethylhydantoin (DMH) (available from BioLab Inc.) with 458 grams of water using a high shear mixer as described in Example 2. This preparation has a very thick consistency.

The dissolution rate of the BCDMH in this preparation was determined as described in Example 2. The calculated time to reach 90% of the nominal concentration was 2.3 minutes with a good fit ($R^2$ 0.97). This preparation exhibited dissolution rates slightly slower than the preparation from Example 5.

Accelerated storage stability was determined for this preparation as described in Example 2. For this preparation the relative activity loss was 10.1% at 15 days and 17.9% at 30 days. This result shows some improvement at 15 days with respect to Example 5, there was no improvement at 30 days over the result from Example 5.

The efficacy of this preparation was tested as described in Example 5. The results are given below in Table 4.

TABLE 4

Efficacy Comparison: BCDMH Powder and Example 6

| | | Number of Tubes (Out of 5) Exhibiting Growth | | | | | | | |
|---|---|---|---|---|---|---|---|---|---|
| ppm † | | E. coli | | | | Strep. Faecalis | | | |
| Total Halogen | BCDMH Treatment | 30 sec | 60 sec | 120 sec | 180 sec | 30 sec | 60 sec | 120 sec | 180 sec |
| 0.0 | None | 5 | 5 | 5 | 5 | 5 | 5 | 5 | 5 |
| 0.1 | Powder | 5 | 5 | 5 | 5 | 5 | 5 | 5 | 5 |
| 0.3 | Powder | 5 | 5 | 5 | 5 | 5 | 5 | 4 | 1 |
| 0.6 | Powder | 0 | 0 | 0 | 0 | 0 | 0 | 0 | 0 |
| 0.9 | Powder | 0 | 0 | 0 | 0 | 0 | 0 | 0 | 0 |
| 0.1 | Example 6 | 5 | 5 | 5 | 5 | 5 | 5 | 5 | 5 |
| 0.3 | Example 6 | 5 | 5 | 5 | 5 | 5 | 5 | 5 | 5 |
| 0.6 | Example 6 | 0 | 0 | 0 | 0 | 0 | 0 | 0 | 0 |
| 0.9 | Example 6 | 0 | 0 | 0 | 0 | 0 | 0 | 0 | 0 |

† ppm expressed as $Cl_2$ - BCDMH Powder results are also found in Example 1

The addition of DMH did improve accelerated storage stability performance for the 15 day period. However, the improvement was not observed at 30 days. The efficacy of this preparation is equal that observed in Example 5, therefore. the added DMH did not adversely effect the biocidal performance of the preparation. The dissolution behavior was similar (or slightly slower) than Example 5 indicating that the added DMH did not have a significant effect.

EXAMPLE 7

The dissolution rate, accelerated storage stability and biocidal efficacy of a 40% BCDMH preparation was determined. The method was similar to that of Example 5 except that the synthetic alumina level was increased in an attempt to improve accelerated storage stability performance.

A preparation was made by mixing 417 grams of Bromi-Cide Powder, 3 grams of monobasic potassium phosphate ($KH_2PO_4$), 3 grams of the Laponite® RD and 9 grams of Laponite® RDS (both synthetic hectorite clay thickening and suspending agents available from Southern Clay Products), and 30 grams of Dispal® 23N4-80 (a synthetic alumina thickening and dispersing agent available from Condea-Vista) with 538 grams of water using a high shear mixer as described in Example 2.

The dissolution rate of the BCDMH in this preparation was determined as described in Example 2. The calculated time to reach 90% of the nominal concentration was 4.2 minutes with a good fit ($R^2$=0.97). This preparation exhibited dissolution rates slower than the preparation from Example 5 and slower than the preparation from Example 4 where the only thickening dispersing agent used was synthetic alumina. The dissolution rate is similar to wetted powder described in Example 2.

Accelerated storage stability was determined for this preparation as described in Example 2. For this preparation the relative activity loss was 12.7% at 15 days and 17.6% at 30 days. This result shows results equivalent to Example 5 so the increased level of synthetic alumina did not improve accelerated storage stability performance compared to Example 5.

The efficacy of this preparation was tested as described in Example 5. The results are given below in Table 5.

TABLE 5

Efficacy Comparison: BCDMH Powder and Example 7

| | | Number of Tubes (Out of 5) Exhibiting Growth | | | | | | | |
|---|---|---|---|---|---|---|---|---|---|
| ppm † | | E. coli | | | | Strep. Faecalis | | | |
| Total Halogen | BCDMH Treatment | 30 sec | 60 sec | 120 sec | 180 sec | 30 sec | 60 sec | 120 sec | 180 sec |
| 0.0 | None | 5 | 5 | 5 | 5 | 5 | 5 | 5 | 5 |
| 0.1 | Powder | 5 | 5 | 5 | 5 | 5 | 5 | 5 | 5 |
| 0.3 | Powder | 5 | 5 | 5 | 5 | 5 | 5 | 4 | 1 |
| 0.6 | Powder | 0 | 0 | 0 | 0 | 0 | 0 | 0 | 0 |
| 0.9 | Powder | 0 | 0 | 0 | 0 | 0 | 0 | 0 | 0 |
| 0.1 | Example 7 | 5 | 5 | 5 | 5 | 5 | 5 | 5 | 5 |
| 0.3 | Example 7 | 5 | 5 | 5 | 5 | 5 | 5 | 5 | 5 |
| 0.6 | Example 7 | 0 | 0 | 0 | 0 | 0 | 0 | 0 | 0 |
| 0.9 | Example 7 | 0 | 0 | 0 | 0 | 0 | 0 | 0 | 0 |

† ppm expressed as $Cl_2$ - BCDMH Powder results are also found in Example 1

The additional synthetic alumina did not improve accelerated storage stability performance compared to the preparation from Example 5. The dissolution rate was slower than when either the synthetic clay or the synthetic alumina were used alone, approximately the same as wetted powder form Example 2. This behavior did not appear to effect BCDMH release at use level determined by measuring biocidal efficacy. As shown in Table 5, performance was equivalent to preparations from Examples 5 and 6 and very similar to dissolved BCMDH Powder.

EXAMPLE 8

The dissolution rate, accelerated storage stability and ease of pumping a 40% BCDMH preparation were determined.

A preparation was made by mixing 417 grams of Bromi-Cide Powder, 3 grams of monobasic potassium phosphate ($KH_2PO_4$) and 40 grams of the Van-Gel-O (available from Vanderbilt), a natural smectite clay thickening and suspending agent, with 540 grams of water using a high shear mixer as described in Example 2.

The dissolution rate of the BCDMH in this preparation was determined as described in Example 2. The calculated time to reach 90% of the nominal concentration was 6.7 minutes with a good fit ($R^2$=0.97). This preparation exhibited dissolution rates slower than the wetted powder preparation described in Example 2.

Accelerated storage stability was determined for this preparation as described in Example 2. For this preparation the relative activity loss was 2.9% at 15 days and 7.3% at 30 days. This result shows superior stability when compared with the preparation from Example 4 where synthetic alumina was the only thickening and dispersing agent.

Pumping performance was tested using a diaphragm metering pump in suction lift mode as described in Example 2. The flow of material was consistent throughout the pump test. There was not separation noted during the test period.

This preparation gave excellent pumping results, with consistent flow and no separation indicating very good dispersion stability. This preparation exhibited excellent performance in the accelerated storage stability test, superior to the alumina only preparation described in Example 4. The dissolution rate was slower than the wetted powder from Example 2 indicating that the clay is not inhibiting the release of BCDMH on dilution.

EXAMPLE 9

The dissolution rate, accelerated storage stability and ease of pumping a 40% BCDMH preparation were determined. This preparation was similar to the preparation described in Example 8 except that the natural clay level was decreased in an attempt to improve dissolution rate performance.

A preparation was made by mixing 417 grams of Bromi-Cide Powder, 3 grams of monobasic potassium phosphate ($KH_2PO_4$) and 30 grams of the Van-Gel-O (available from Vanderbilt), a natural smectite clay thickening and suspending agent, with 550 grams of water using a high shear mixer as described in Example 2.

The dissolution rate of the BCDMH in this preparation was determined as described in Example 2. The calculated time to reach 90% of the nominal concentration was 0.8 minutes with a good fit ($R^2=0.94$). This preparation exhibited dissolution rates more rapid than observed with the preparation from Example 3 where the synthetic clay was the only thickening and dispersing agent.

Accelerated storage stability was determined for this preparation as described in Example 2. For this preparation the relative activity loss was 3.8% at 15 days and 8.1% at 30 days. The reduction in natural clay level resulted in a slight reduction in performance as measured by this test. This result is similar to the preparation from Example 4 where synthetic alumina was the only thickening and dispersing agent.

Pumping performance was tested using a diaphragm metering pump in suction lift mode as described in Example 2. The flow of material was consistent throughout the pump test. There was not separation noted during the test period.

Reducing the natural clay level in this preparation, compared to the preparation from Example 8, resulted in significant improvement in dissolution rate. However, this reduction in thickening and dispersion agent level did not degrade the excellent pumping performance observed with the preparation from Example 8. Accelerated storage stability performance of this preparation was slightly lower for this preparation than for the preparation described in Example 8. However, they were comparable to the alumina only preparation described in Example 4.

EXAMPLE 10

The practical utility of these preparations was demonstrated by treating an open recirculating cooling water system with the preparation described in Example 9.

The 47,000 gallon capacity system was continuously treated for several years with BromiCide® Tablets (approximately 96% BCMDH, available from BioLab, Inc.) using a bypass feeder at a use rate of approximately 160 pounds of tablets per week. This yielded an average free halogen residual of 0.19 ppm (expressed as $Cl_2$) with a measured range of 0.12 to 0.34 ppm (expressed as $Cl_2$). Adjusting the flow of system water through the bypass feeder and maintaining the level of tablets in the bypass feeder controlled the feed rate. The water flow rate varied between two and three gallons per minute depending on temperature and tablet bed level. For consistent control, the bypass feeder was filled several times per week. The actual usage rate during the monitoring period was 157 to 163 pounds of tablets per week.

This system was then treated with the preparation described in Example 9 by pumping product, in suction lift mode, from a 55 gallon drum into the system using a diaphragm pump (pump model—Alpha 080NP6060D0, available from ProMinent Fluid Controls Inc.). The product discharged from the pump was mixed with one gallon per minute of system water using an in-line mixer (motionless mixer model number ¾-80-4-6-2, available from Koflo Corporation). The product feed rate was controlled by pump rate adjustment (set to 0.8 gallons per hour, specific gravity is 1.2) along with an interval timer (set for 3 minutes on and 7 minutes off). This feed rate is equivalent to 161.5 pounds of BCDMH fed per week. This yielded an average free halogen residual of 0.21 ppm (expressed as $Cl_2$) with a measured range of 0.13 to 0.25 ppm (expressed as $Cl_2$).

This Example demonstrates the practical advantages associated with these preparations. By pumping the active ingredient in liquid form, less manpower was required to service the bypass feeder with respect to adjusting system water flow rates and filling with tablets. Using the liquid product also eliminated exposure to dust associated with emptying pails of tablets into the bypass feeder. The in-line mixer was included in the feed system because there was not a convenient turbulent area for direct product feed. Only one gallon per minute of system water was used with the in-line mixer, which was not optimized, to pre-disperse the product compared with the two to three gallons per minute used to dissolve the product in the bypass feeder. Equivalent feed rate of active ingredient, BCDMH, into the system using either pre-dissolved tablets delivered via a bypass feeder or feed of a thickened suspension, described in Example 9, delivered with a pump resulted in equivalent measured residuals. This confirms the laboratory testing results demonstrating that these suspension release active ingredient on dilution to use levels.

EXAMPLE 11

The dissolution rate, accelerated storage stability and biocidal efficacy of a terbuthylazine preparation was determined. The method was similar to that of Example 7 except that the dispersed agent was terbuthylazine rather than BCDMH.

A preparation was made by mixing 417 grams of Bellacide® 320 (96% terbuthylazine, available from FMC Corporation), 3 grams of monobasic potassium phosphate ($KH_2PO_4$), 3 grams of the Laponite® RD and 9 grams of Laponite® RDS (both synthetic hectorite clay thickening and suspending agents available from Southern Clay Products), and 30 grams of Dispal® 23N4-80 (a synthetic alumina thickening and dispersing agent available from Condea-Vista) with 538 grams of water using a high shear mixer as described in Example 2.

The dissolution rate of terbuthylazine was determined as described in Examples 1 and 2 except that the target nominal solution concentration was 4 ppm terbuthylazine rather than the 400 ppm BCDMH. Terbuthylazine concentrations were determined by HPLC. Terbuthylazine dissolution rates are reported in Table 6 for Bellacide 320 powder, Bellacide® 325 liquid (a 4% aqueous terbuthylazine dispersion available from FMC Corporation) and this preparation. 90% dissolution was achieved in approximately 21 hours for powder, 3½ hours for Bellacide® 325 and a little more than 2 hours for the preparation described in this example. The data fit was fair for powder and good for Bellacide® 325 and the preparation from this example.

TABLE 6

Terbuthylazine Dissolution Rates, 4 ppm Nominal Concentration

|  | Bellacide 320 powder | Bellacide 325 Liquid | Preparation from Example 11 |
| --- | --- | --- | --- |
| Time to 90% Dissolution (Minutes) | 1271 | 210 | 130 |
| $R^2$ | 0.86 | 0.97 | 0.99 |

Accelerated storage stability was determined for this preparation as described in Example 2 except that the active ingredient was determined by HPLC. For this preparation the relative activity loss was 3.2% at 30 days. This result is consistent with the good hydrolytic stability associated with terbuthylazine.

The algicidal efficacy was determined for Terbuthylazine in the form of Bellacide 320 powder, Bellacide 325 and the preparation described in this example. A test culture of *Chlorella pyrenoidosa* was prepared by incubating cells in Allen's media with 16 hours of fluorescent light per day. Cells were counted and standardized such that they could be added to test flasks to achieve a level of 300,000 cells/ml to yield a light green color. The test flasks, prior to inoculation, contained Allen's media treated with the desired level of terbuthylazine from either Bellacide 320 powder, Bellacide 325 or the preparation described in this example. The treated, inoculated test flasks were observed while being kept under 16 hours of fluorescent light per day for 10 days. Flasks were observed for algae growth as indicated by a green color. The results of this testing are given in Table 7. In each case the there was growth noted at 1 ppm or less and no growth noted when terbuthylazine was present at 2 ppm.

TABLE 7

Terbuthylazine Algae Efficacy Comparison

| Nominal Terbuthylazine Concentration | Bellacide 320 powder | Bellacide 325 Liquid | Preparation from Example 11 |
| --- | --- | --- | --- |
| 0.25 ppm | Growth | Growth | Growth |
| 0.50 ppm | Growth | Growth | Growth |
| 1.00 ppm | Growth | Growth | Growth |
| 2.00 ppm | No Growth | No Growth | No Growth |

This example demonstrates that different substances can realize similar benefits from formulation with the thickening and dispersing agents. In this example a preparation was made as described in Example 7 except that 40% terbuthylazine was substituted for 40% BCDMH. The dissolution rate of this 40% preparation was superior to the 4% commercial liquid dispersion, Bellacide 325. The efficacy of the active ingredient was not effected in this preparation. The excellent accelerated storage stability was expected because terbuthylazine is hydrolytically stable.

EXAMPLE 12

The dissolution rate, accelerated storage stability and ease of pumping of a terbuthylazine preparation was determined. The method was similar to Example 8 except that the dispersed agent was terbuthylazine rather than BCDMH.

A preparation was made by mixing 417 grams of Bellacide® 320 (96% terbuthylazine, available from FMC Corporation), 3 grams of monobasic potassium phosphate ($KH_2PO_4$) and 40 grams of the Van-Gel-O (available from R.T. Vanderbilt Company Inc.), a natural smectite clay thickening and suspending agent, with 540 grams of water using a high shear mixer as described in Example 2.

The dissolution rate of the terbuthylazine in this preparation was determined as described in Example 11. The calculated time to reach 90% of the nominal concentration was 79 minutes with a good fit ($R^2$=0.99). This preparation exhibited dissolution rates even faster than the preparation described in Example 11.

Accelerated storage stability was determined for this preparation as described in Example 11. For this preparation the relative activity loss was 1.0% at 30 days. This result is consistent with the good hydrolytic stability associated with terbuthylazine.

Pumping performance was tested using a diaphragm metering pump in suction lift mode as described in Example 2. The material would not flow over the entire length of the test.

This preparation improved on the dissolution rate over the preparation in Example 11. It appeared that the reason that the pump could not maintain flow was that the consistency was too thick. The excellent accelerated storage stability was expected because terbuthylazine is hydrolytically stable.

EXAMPLE 13

The ease of pumping of a preparation similar to Example 12 was determined. The procedure was similar to that of Example 12 except that the level of dispersing and thickening agent was reduced from 4.0% to 3.0%.

A preparation was made by mixing 417 grams of Bellacide® 320 (96% terbuthylazine, available from FMC Corporation), 3 grams of monobasic potassium phosphate ($KH_2PO_4$) and 30 grams of the Van-Gel-O (available from R.T. Vanderbilt Company Inc.), a natural smectite clay thickening and suspending agent, with 550 grams of water using a high shear mixer as described in Example 2.

Pumping performance was tested using a diaphragm metering pump in suction lift mode as described in Example 2. The flow of material was consistent throughout the pump test with no separation.

Reducing the level of dispersing and thickening agent from 4.0% in Example 12 to 3.0% in this example resulted in excellent pumping performance. This is probably because this preparation was thinner in consistency than the preparation described in Example 12 making the material easier to pump.

EXAMPLE 14

The ease of pumping of a preparation similar to Example 13 was determined. The method was similar to that of Example 13 except that 1.0% of a fumed silica thickening and dispersing agent was used instead of 3.0% of a natural clay.

A preparation was made by mixing 417 grams of Bellacide® 320 (96% terbuthylazine, available from FMC Corporation), 3 grams of monobasic potassium phosphate ($KH_2PO_4$) and 10 grams of Cabosil M-5 (available from Cabot Corporation, a fumed silica thickening and suspending agent), with 570 grams of water using a high shear mixer as described in Example 2.

Pumping performance was tested using a diaphragm metering pump in suction lift mode as described in Example 2. The flow of material was consistent throughout the pump test with no separation.

The results from this Example demonstrate that fumed silica dispersing and thickening agents can also be used to make preparations which exhibit excellent pumping performance.

EXAMPLE 15

The dissolution rate, and accelerated storage stability of a preparation similar to Example 7 was determined. The method was similar to that of Example 7 except that the dispersed agent was 2-(2-bromo -2-nitro)-ethenyl furan (BNEF) rather than BCDMH.

A preparation was made by mixing 400 grams of BNEF solid which had been ground in a mortar and pestle (99% BNEF prepared as described in U.S. Pat. No. 5,138,076), 3 grams of monobasic potassium phosphate ($KH_2PO_4$), 3 grams of the Laponiteo® RD and 9 grams of Laponite® RDS (both synthetic hectorite clay thickening and suspending agents available from Southern Clay Products), and 30 grams of Dispal® 23N4-80 (a synthetic alumina thickening and dispersing agent available from Condea-Vista) with 555 grams of water using a high shear mixer as described in Example 2.

Figure 2:
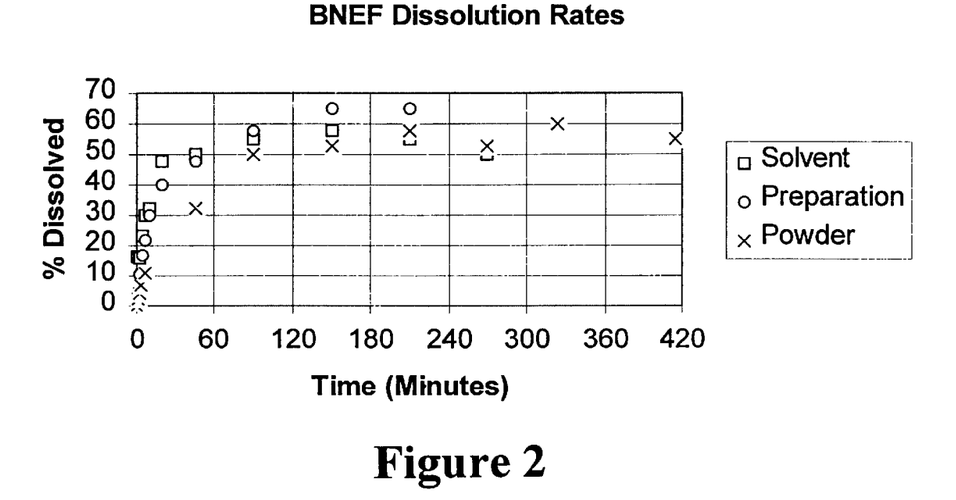
FIG. 2 shows the dissolution rate of BNEF.

The dissolution rate of BNEF was determined as described in Examples 1 and 2 except that the target nominal solution concentration was 40 ppm BNEF rather than the 400 ppm BCDMH. Terbuthylazine concentrations were determined by HPLC. BNEF dissolution rates are shown in FIG. 2 for BNEF solid which had been ground in a mortar and pestle (99% BNEF prepared as described in U.S. Pat. No. 5,138,076), a 10% solution of BNEF dissolved in the organic solvent, propylene carbonate, as described in U.S. Pat. No. 5,122,301 and the preparation described in this Example. 90% dissolution was not achieved in any of these tests probably because BNEF hydrolyzes in water at a rate which was similar to the dissolving rate. The solid did not dissolve as rapidly as either liquid formulation. The dissolution rate of the preparation described in this example was similar to, to slightly more rapid than, that of the organic solvent, based formulation. This equivalent dissolution rate was achieved without contaminating the waste system with organic solvent.

Accelerated storage stability was determined for this preparation as described in Example 2 except that the active ingredient was determined by HPLC. For this preparation the relative activity loss was 20% at 30 days. This is a higher than the 4.1% activity loss for the 10% solution of BNEF dissolved in the organic solvent, propylene carbonate, reported in U.S. Pat. No. 5,122,301. The activity loss is probably due to the rapid hydrolysis of BNEF in water.

EXAMPLE 16

The dissolution rate, and accelerated storage stability of a preparation similar to Example 7 was determined. The method was similar to that of Example 7 except that the dispersed agent was isocyanuric acid (CYA) rather than BCDMH.

A preparation was made by mixing 400 grams of CYA granules which had been ground in a mortar and pestle (100% Isocyanuric Acid granules [4 to 10 mesh particle size] from Delcal Inc.), 3 grams of monobasic potassium phosphate ($KH_2PO_4$), 3 grams of the Laponite® RD and 9 grams of Laponite® RDS (both synthetic hectorite clay thickening and suspending agents available from Southern Clay Products), and 30 grams of Dispal® 23N4-80 (a synthetic alumina thickening and dispersing agent available from Condea-Vista) with 555 grams of water using a high shear mixer as described in Example 2.

The dissolution rate of CYA was determined as described in Examples 1 and 2 with a target nominal solution concentration of 400 ppm CYA. CYA concentrations were determined by HPLC. CYA dissolution rates are reported in Table 7 for Isocyanuric Acid granules and this preparation. 90% dissolution was achieved in 35 minutes for granules and 5 minutes for the preparation described in this example. The data fit was good for both the granules and the preparation from this example.

TABLE 8

Isocyanuric Acid Dissolution Rates, 400 ppm Nominal Concentration

|  | Isocyanuric Acid granules | Preparation from Example 16 |
| --- | --- | --- |
| Time to 90% Dissolution (Minutes) | 35 | 5 |
| $R^2$ | 0.94 | 0.97 |

Accelerated storage stability was determined for this preparation as described in Example 2 except that the active ingredient was determined by HPLC. For this preparation the relative activity loss was 3.2% at 30 days. This result is consistent with the good hydrolytic stability associated with CYA.

This example demonstrates that substances other than biocides can realize similar benefits from formulation with the thickening and dispersing agents. In this example a preparation was made as described in Example 7 except that 40% CYA was substituted for 40% BCDMH. The dissolution rate of this 40% preparation was much more rapid than CYA in granular form. The excellent accelerated storage stability was expected because terbuthylazine is hydrolytically stable.

EXAMPLE 17

The dissolution rate and accelerated storage stability of a preparation similar to Example 8 was investigated. The method was similar to that of Example 8 except that the dispersed agent was methyene-bis-thiocyanate rather than BCDMH.

A preparation is made by mixing 400 grams of methyene-bis-thiocyanate, 3 grams of monobasic potassium phosphate ($KH_2PO_4$) and 40 grams of the Van-Gel-O (available from R.T. Vanderbilt Company Inc.), a natural smectite clay thickening and suspending agent, with 557 grams of water using a high shear mixer as described in Example 2.

The dissolution rate of the methyene-bis-thiocyanate in this preparation is determined as described in Example 11, and is found to be significantly faster than the dissolution rate of the base compound.

Accelerated storage stability is determined for this preparation as described in Example 11. The composition displays good hydrolytic stability.

EXAMPLE 18

The dissolution rate and accelerated storage stability of a preparation similar to Example 8 was investigated. The method was similar to that of Example 8, except that the dispersed agent was bromonitrostyrene rather than BCDMH.

A preparation is made by mixing 400 grams of bromonitrostyrene, 3 grams of monobasic potassium phosphate ($KH_2PO_4$) and 40 grams of the Van-Gel-O (available from R.T. Vanderbilt Company Inc.), a natural smectite clay thickening and suspending agent, with 557 grams of water using a high shear mixer as described in Example 2.

The dissolution rate of the bromonitrostyrene in this preparation is determined as described in Example 11, and is found to be significantly faster than the dissolution rate of the base compound.

Accelerated storage stability is determined for this preparation as described in Example 11. The composition displays good hydrolytic stability.

EXAMPLE 19

The dissolution rate and accelerated storage stability of a preparation similar to Example 8 was investigated. The method was similar to that of Example 8, except that the dispersed agent was TCCA rather than BCDMH.

A preparation is made by mixing 400 grams of TCCA, 3 grams of monobasic potassium phosphate ($KH_2PO_4$) and 40 grams of the Van-Gel-O (available from R.T. Vanderbilt Company Inc.), a natural smectite clay thickening and suspending agent, with 557 grams of water using a high shear mixer as described in Example 2.

The dissolution rate of the TCCA in this preparation is determined as described in Example 11, and is found to be significantly faster than the dissolution rate of the base compound.

Accelerated storage stability is determined for this preparation as described in Example 11. The composition displays good hydrolytic stability.

EXAMPLE 20

The dissolution rate and accelerated storage stability of a preparation similar to Example 8 was investigated. The method was similar to that of Example 8, except that the dispersed agent was calcium hypochlorite instead of BCDMH.

A preparation is made by mixing 400 grams of calcium hypochlorite, 3 grams of monobasic potassium phosphate ($KH_2PO_4$) and 40 grams of the Van-Gel-O (available from R.T. Vanderbilt Company Inc.), a natural smectite clay thickening and suspending agent, with 557 grams of water using a high shear mixer as described in Example 2.

The dissolution rate of the calcium hypochlorite in this preparation is determined as described in Example 11, and is found to be significantly faster than the dissolution rate of the base compound.

Accelerated storage stability is determined for this preparation as described in Example 11. The composition displays good hydrolytic stability.

EXAMPLE 21

The dissolution rate and accelerated storage stability of a preparation similar to Example 8 was investigated. The method was similar to that of Example 8, except that the dispersed agent was dibromodimethylhydantoin rather than BCDMH.

A preparation is made by mixing 400 grams of dibromodimethylhydantoin, 3 grams of monobasic potassium phosphate ($KH_2PO_4$) and 40 grams of the Van-Gel-O (available from R.T. Vanderbilt Company Inc.), a natural smectite clay thickening and suspending agent, with 557 grams of water using a high shear mixer as described in Example 2.

The dissolution rate of the dibromodimethylhydantoin in this preparation is determined as described in Example 11, and is found to be significantly faster than the dissolution rate of the base compound.

Accelerated storage stability is determined for this preparation as described in Example 11. The composition displays good hydrolytic stability.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. A method of improving the rate of dissolution in water of a low solubility compound, said method comprising:

(a) combining a low solubility compound with water and a rheology additive to form an aqueous suspension comprising 1% to 80% of said low solubility compound, wherein said rheology additive comprises platelets or particles which orient together with ionic or hydrogen bonds to form a three-dimensional structure; and (b) adding said suspension to water and allowing the low solubility compound to dissolve in the water.

2. The method of claim 1 wherein said combining step combines the low solubility compound with water and an amount of rheology additive sufficient to provide 0.5% to 5.0% rheology additive in the aqueous suspension.

3. The method of claim 1 wherein said low solubility compound comprises a member selected from the group consisting of low solubility halogenated hydantoins, halogenated isocyanuric acids, halogenated furans, halogenated styrenes, s-triazines, cyanuric acid, solid metal hypohalites, and thiocyanates.

4. The method of claim 3 wherein said low solubility compound is a halogenated hydantoin.

5. The method of claim 4 wherein said halogenated hydantoin is BCDMH.

6. The method of claim 4 wherein said halogenated hydantoin is DBDMH.

7. The method of claim 4 wherein said halogenated hydantoin is DCDMH.

8. The method of claim 4 wherein said halogenated hydantoin is DCMEH.

9. The method of claim 3 wherein said low solubility compound is a halogenated isocyanuric acid.

10. The method of claim 3 wherein said halogenated isocyanuric acid is TCCA.

11. The method of claim 9 wherein said halogenated isocyanuric acid is DCCA.

12. The method of claim 3 wherein said low solubility compound is a solid metal hypohalite.

13. The method of claim 3 wherein said solid metal hypohalite is calcium hypochlorite.

14. The method of claim 1 wherein said low solubility compound is a halogenated furan.

15. The method of claim 14 wherein said halogenated furan is BNEF.

16. The method of claim 1 wherein said low solubility compound is a halogenated styrene.

17. The method of claim 16 wherein said halogenated styrene is BNS.

18. The method of claim 1 wherein said low solubility compound is cyanuric acid.

19. The method of claim 1 wherein said low solubility compound is an s-triazine.

20. The method of claim 19 wherein said s-triazine is terbuthylazine.

21. The method of claim 1 wherein said low solubility compound is a thiocyanate.

22. The method of claim 21 wherein said thiocyanate is MBT.

23. The method of claim 1 wherein said rheology additive comprises a natural or synthetic clay.

24. The method of claim 23 wherein said natural or synthetic clay comprises a synthetic smectite.

25. The method of claim 23 wherein said natural or synthetic clay comprises a natural smectite.

26. The method of claim 1 wherein said rheology additive comprises a natural or synthetic silica.

27. The method of claim 1 wherein said rheology additive comprises a natural or synthetic alumina.

28. The method of claim 1 wherein said rheology additive comprises an organic dispersant.

29. The method of claim 1 wherein said aqueous suspension comprises 10% to 80% of said low solubility compound and 0.1% to 10% of said rheology additive.

30. A method of improving the hydrolytic stability of a hydrolytically unstable compound, the method comprising combining a hydrolytically unstable compound with water and a rheology additive to form an aqueous suspension comprising 1% to 80% of said hydrolytically unstable compound; wherein said rheology additive comprises platelets or particles which orient together with ionic or hydrogen bonds to form a three-dimensional structure.

31. The method of claim 30 wherein said aqueous suspension comprises 10% to 80% of said hydrolytically unstable compound and 0.1% to 10% of said rheology additive.

32. An aqueous suspension comprising 1% to 80% of a low solubility compound, 0.1 to 10% of a rheology additive, and water; wherein said rheology additive comprises platelets or particles that orient together with ionic or hydrogen bonds, and wherein said low solubility compound is present in an amount at least as great as the amount of rheology additive.

33. The aqueous suspension of claim 32 wherein said low solubility compound comprises a member selected from the group consisting of low solubility halogenated hydantoins, halogenated isocyanuric acids, halogenated furans, halogenated styrenes, s-triazines, cyanuric acid, solid metal hypohalites, and thiocyanates.

34. The aqueous suspension of claim 33 wherein said low solubility compound is a halogenated hydantoin.

35. The aqueous suspension of claim 34 wherein said halogenated hydantoin is BCDMH.

36. The aqueous suspension of claim 34 wherein said halogenated hydantoin is DBDMH.

37. The aqueous suspension of claim 34 wherein said halogenated hydantoin is DCDMH.

38. The aqueous suspension of claim 34 wherein said halogenated hydantoin is DCMEH.

39. The aqueous suspension of claim 33 wherein said low solubility compound is a halogenated isocyanuric acid.

40. The aqueous suspension of claim 39 wherein said halogenated isocyanuric acid is TCCA.

41. The aqueous suspension of claim 39 wherein said halogenated isocyanuric acid is DCCA.

42. The aqueous suspension of claim 33 wherein said low solubility compound is an s-triazine.

43. The aqueous suspension of claim 42 wherein said s-triazine is terbuthylazine.

44. The aqueous suspension of claim 33 wherein said low solubility compound is a halogenated furan.

45. The aqueous suspension of claim 44 wherein said halogenated furan is BNEF.

46. The aqueous suspension of claim 33 wherein said low solubility compound is a halogenated styrene.

47. The aqueous suspension of claim 46 wherein said halogenated styrene is BNS.

48. The aqueous suspension of claim 33 wherein said low solubility compound is cyanuric acid.

49. The aqueous suspension of claim 33 wherein said low solubility compound is a solid metal hypohalite.

50. The aqueous suspension of claim 49 wherein said solid metal hypohalite is calcium hypochlorite.

51. The aqueous suspension of claim 33 wherein said low solubility compound is a thiocyanate.

52. The aqueous suspension of claim 51 wherein said thiocyanate is MBT.

53. The aqueous suspension of claim 32 wherein said rheology additive comprises a natural or synthetic clay.

54. The aqueous suspension of claim 53 wherein said natural or synthetic clay comprises a synthetic smectite.

55. The aqueous suspension of claim 53 wherein said natural or synthetic clay comprises a natural smectite.

56. The aqueous suspension of claim 32 wherein said rheology additive comprises an organic dispersant.

57. The aqueous suspension of claim 32 wherein said suspension comprises 10% to 80% of said low solubility compound and 0.1% to 10% of said rheology additive.

58. The aqueous suspension of claim 32 wherein said rheology additive comprises a natural or synthetic silica.

59. The aqueous suspension of claim 58 wherein said natural or synthetic silica is a fumed silica.

60. The aqueous suspension of claim 32 wherein said rheology additive comprises a natural or synthetic alumina.

* * * * *